United States Patent [19]

Connor et al.

[11] 4,007,205
[45] Feb. 8, 1977

[54] 7-SUBSTITUTED-9-OXOXANTHENE-2-CARBOXALDEHYDES

[75] Inventors: David T. Connor, Parsippany; Max von Strandtmann, Rockaway, both of N.J.

[73] Assignee: Warner-Lambert Company, Morris Plains, N.J.

[22] Filed: Mar. 16, 1976

[21] Appl. No.: 667,922

[52] U.S. Cl. .................................. 260/335; 424/283
[51] Int. Cl.[2] ........................................ C07D 311/86
[58] Field of Search ................................... 260/335

[56] References Cited

UNITED STATES PATENTS 3,706,768  12/1972  Bays .................................. 260/335
3,948,949  4/1976  Gante et al. ........................ 260/335

OTHER PUBLICATIONS

Chemical Abstracts, vol. 51, 12891b.

*Primary Examiner*—Norma S. Milestone
*Attorney, Agent, or Firm*—Albert H. Graddis; Frank S. Chow

[57] ABSTRACT

There are disclosed 7-substituted-9-oxoxanthene-2-carboxaldehydes of the formula:

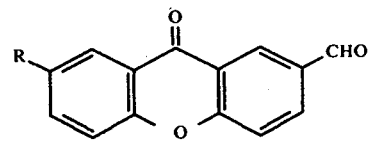

in which R is lower alkoxy or hydroxy. These compounds are indicated in the management of allergic manifestations such as, for example, bronchial asthma or hay fever.

3 Claims, No Drawings

7-SUBSTITUTED-9-OXOXANTHENE-2-CARBOXALDEHYDES

The present invention relates to 7-substituted-9-oxoxanthene-2-carboxyaldehydes having the following structural formula:

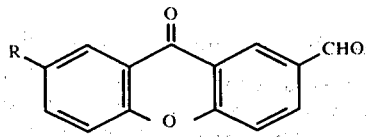

in which R is lower alkoxy of 1-6 carbon atoms or hydroxy. Examples of lower alkoxy are methoxy, ethoxy, proproxy, isopropoxy, butyloxy, isobutyloxy and so on.

Embraced within the scope of the present invention are pharmaceutical compositions containing as active ingredients the above compounds.

The compounds of this invention exhibit antiallergic properties in animal studies. For example, the compound 7-methoxy-9-oxoxanthene-2-carboxaldehydes shows a 100% inhibition of the allergic response at a dose of about 10 mg/kg orally in rats, when tested in the passive cutaneous anaphalaxis screen, which is a modification of procedures described by I. Mota, *Life Sciences*, 7: 465 (1963) and Z. Ovary and O. Bier, *Proc. Soc. Exptl. Biol. Med.*, 81: 585 (1952).

The compounds of this invention are indicated in the management of allergic manifestations such as, for example, bronchial asthma or hay fever. A dose of about 10 mg/kg orally, parenterally or by inhalation two or three times a day is suggested. As with any allergy treatment, the dose must be titrated according to the individual needs by methods known to the healing arts.

Among the oral dosage forms there may be mentioned, for example, tablets, capsules, elixirs and syrup. These are prepared by mixing the active ingredient with an inert pharmaceutical diluent such as lactose, mannitol, simple syrup and formulated into desired dosage forms by methods well known in the pharmacist's art.

For inhalation therapy, the compounds are prepared by procedures used in aerosol technology. See, for example, U.S. Pat. Nos. 2,868,691 and 3,095,355.

According to the present invention, Compound I is prepared by treating a carboxylic acid of the formula:

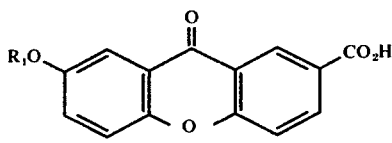

with an esterifying agent such as lower alkanol and sulfuric acid to obtain the corresponding ester of the formula:

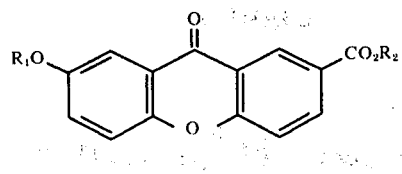

in which $R_1$ is lower alkyl. In a typical process, Compound II is converted to the ester, III, employing ethyl alcohol and concentrated sulfuric acid.

The starting Compound II is disclosed in J. R. Pfister, I. T. Harrison and J. H. Fried, Ger. Patent 2,300,384, and *Chemical Abstract*, 81: 13391a (1974); E. S. K. Assem, *Proc. Roy. Soc. Med.*, 66 (12), 1191-8 (1973): E. S. K. Assem, J. A. Evans and M. McAllen, *Brit. Med. Jour.*, 93-95 (1974).

In the next step the ester, III, is reduced with a complex metal hydride to the corresponding diol of the formula:

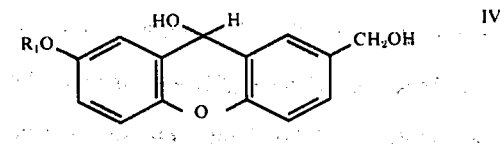

Among the complex metal hydrides which may be mentioned are, for example, lithiumaluminum hydride, sodium or potassium borohydride, and the like.

The diol is thereafter oxidized with Jones' reagent to give those compounds of the invention, I, in which R is lower alkyl.

The compounds of the invention, I, in which R is hydroxy are obtained by dealkylation of those compounds in which R is lower alkoxy, by standard dealkylating techniques. For example, when R is methoxy, it is treated with a hydrogen halide such as hydrogen bromide in acetic acid to obtain the corresponding hydroxy compounds.

In order to illustrate the practice of this invention, the following examples are included.

EXAMPLE 1

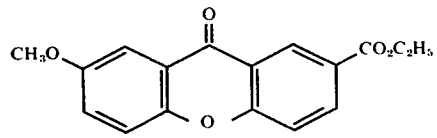

Ethyl 7-methoxy-9-oxoxanthene-2-carboxylate

A mixture of 7-methoxy-9-oxoxanthene-2-carboxylic acid in ethanol (100ml) and concentrated sulfuric acid (10 ml) was refluxed under nitrogen for 24 hours. The reaction mixture was concentrated and cooled. The product, which precipitated, was filtered off and recrystallized from ethanol to give white crystals (2.53g, 84%), mp. 170°-172° C.

Anal. Calcd. for $C_{17}H_{14}O_5$: C, 68.45; H, 4.73. Found: C, 68.20; H, 4.75.

EXAMPLE 2

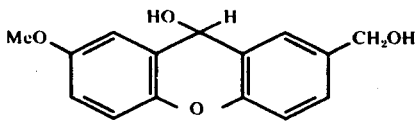

9-Hydroxy-7-methoxy-9H-xanthene-2-methanol

Lithium aluminum hydride (500 mg) was added to a stirred solution of ethyl 7-methoxy-9-oxoxanthene-2-carboxylate (1g) in THF (100 ml). The reaction mixture was stirred at room temperature under nitrogen for 5 hours. Water and MgSO$_4$ were added. The inorganic solids were filtered off and washed with ethyl acetate. The filtrate and washings were combined and evaporated to give the crude product. Recrystallization from ethyl acetate gave white crystals (0.82 g, 84%), mp. 142°–143°.

Anal. Calcd. for $C_{15}H_{14}O_4$: C, 69.75; H, 5.46. Found: C, 69.66; H, 5.49.

EXAMPLE 3

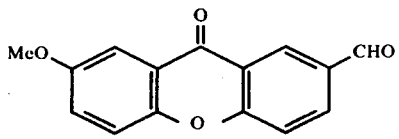

7-Methoxy-9-oxoxanthene-2-carboxaldehyde

8N Jones' reagent (2ml) in acetone (13 ml) was added dropwise to a stirred solution of 9-hydroxy-7-methoxy-9H-xanthene-2-methanol (4.4 g) until thin-layer chromatography indicated the reaction was complete. A few drops of isopropanol were added to decompose any excess reagent. The inorganic salts were filtered off and washed with acetone. The acetone was evaporated at reduced pressure, and the residue was partitioned between water and CHCl$_3$. The CHCl$_3$ extracts were dried over MgSO$_4$ and evaporated to give yellow crystals. Recrystallization from ethyl acetate gave crystals (3.49 g, 79%), mp. 167°–169°.

Anal. Calcd. for $C_{15}H_{10}O_4$: C, 70.86; H, 3.96. Found: C, 70.70; H, 4.11.

We claim:
1. A compound of the formula:

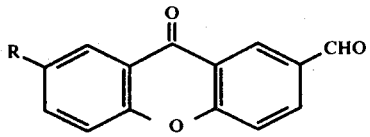

in which R is lower alkoxy or hydroxy.

2. A compound according to claim 1 which is 7-methoxy-9-oxoxanthene-2-carboxyaldehyde.
3. 9-hydroxy-7-methoxy-9H-xanthene-2-methanol.

* * * * *